(12) United States Patent
Odanaka et al.

(10) Patent No.: US 7,326,052 B2
(45) Date of Patent: Feb. 5, 2008

(54) DENTAL SHADE GUIDE HAVING TAG WITH MARK INDICATION PART

(75) Inventors: Yasuhiro Odanaka, Tokyo (JP); Tetsuro Sakuma, Tokyo (JP); Mizuki Nakayama, Tokyo (JP); Daiki Machida, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 11/158,073

(22) Filed: Jun. 22, 2005

(65) Prior Publication Data

US 2005/0287489 A1 Dec. 29, 2005

(30) Foreign Application Priority Data

Jun. 25, 2004 (JP) .............................. 2004-187414

(51) Int. Cl.
*A61C 19/10* (2006.01)
(52) U.S. Cl. ..................................... 433/26; 433/203.1
(58) Field of Classification Search .................. 433/26, 433/203.1, 163, 199.1, 171; D24/176
See application file for complete search history.

(56) References Cited

U.S. PATENT DOCUMENTS

| 785,992 | A | * | 3/1905 | Whiteley ..................... 433/26 |
| 1,327,306 | A | | 1/1920 | Berger | |
| 1,713,267 | A | * | 5/1929 | Crowley ................. 433/203.1 |
| 1,744,043 | A | * | 1/1930 | Grant ...................... 433/203.1 |
| 2,805,478 | A | * | 9/1957 | Adams ......................... 433/26 |
| 3,964,167 | A | | 6/1976 | Yerkes | |
| 4,919,616 | A | * | 4/1990 | Croll ............................ 433/26 |
| 4,919,617 | A | | 4/1990 | Antons et al. | |
| 5,066,227 | A | * | 11/1991 | Pozzi .......................... 433/26 |
| 5,257,931 | A | | 11/1993 | Pozzi | |
| 5,989,022 | A | * | 11/1999 | Yamamoto et al. ........... 433/26 |
| 6,139,318 | A | * | 10/2000 | Foser .......................... 433/26 |

FOREIGN PATENT DOCUMENTS

| DE | 100 51 750 A1 | 5/2002 |
| EP | 1 002 504 A2 | 5/2000 |
| JP | 2003-513743 | 4/2003 |
| WO | WO 01/35855 A1 | 5/2001 |

* cited by examiner

*Primary Examiner*—Cris Rodriguez
*Assistant Examiner*—Candice C Stokes
(74) *Attorney, Agent, or Firm*—Oblon, Spivak, McClelland, Maier & Neustadt, P.C.

(57) ABSTRACT

To photograph teeth and dental shade guides including marks indicating color tones of a color samples together in large size and particularly, without making the photographing distance far from the teeth, irrespective of the color samples to plate-shaped handle parts, in the dental shade guide, has a color sample modeling a form of an artificial tooth of an anterior tooth and a tag having a mark indication part are attached at one end of a plate-shaped handle part rotatably around an axis, the tag is attached at a lingual surface side of the color sample, and the mark indication part protrudes 1 to 15 mm at the maximum only from a tooth root directional end or side of the color sample.

2 Claims, 4 Drawing Sheets

DENTAL SHADE GUIDE HAVING TAG WITH MARK INDICATION PART

BACKGROUND OF THE INVENTION

1. Field of the Invention

The present invention relates to a dental shade guide, which is used for selecting a color tone having excellent aesthetic property when making a dental prosthesis.

2. Description of the Conventional Art

When a material having the excellent aesthetic property, such as a dental porcelain or the like, is used as the dental prosthesis, a dentist enters a color of a tooth of a patient in a written directive, and directs a dental technician to make the dental prosthesis having the same color as the tooth of a patient. In order to give more particular information to the technician, the tooth of a patient and color samples of teeth may be simultaneously photographed by a camera such as a digital camera or the like, and this photograph is sent to the technician. This color sample is called a dental shade guide. In the photograph, a plurality of the dental shade guides having different color tones and the tooth of a patient are simultaneously photographed, and the color tone of a patient is visually given to the technician actually making the prosthesis from this photograph. Thus, the technician can make the dental prosthesis referring to the color tones of the plurality of the dental shade guides in the photograph.

However, the conventional dental shade guide has a shape in which the color sample models a form of an artificial tooth of an anterior tooth and is attached to one end of a plate-shaped handle part so as to be rotatable around an axis (hereinafter, this color sample is referred to as the color sample). In many cases, a dental shade guides have a neck part where a width of the handle part at the one end side is thinly formed and the color sample is attached. Further, a mark such as A2, C3 or the like showing the color tone of the color sample is indicated at a position where this mark can be confirmed however the color sample may be rotated. That is, this mark is indicated at the handle part under the main part being away from the color sample in many cases (for example, refer to published Japanese translations of PCT international publication for patent applications Ser. No. 2003-513743, FIG. 3, U.S. Pat. No. 4,919,617, and U.S. Pat. No. 5,257,931).

In such the conventional dental shade guide, the mark showing the color tone of the color sample is indicated away from the color sample. Thus, for example, as shown in FIG. 1, when the plurality of the dental shade guides photographed simultaneously with a plurality of teeth T of a patient, it is necessary to photograph these teeth T and dental shade guides having marks M showing the color tones of color samples 2 within a frame of the photograph. Thus, since a photographing distance from the tooth of a patient is made far, there is a problem that the teeth and the dental shade guides cannot be photographed in a large size and particularly.

Further, as shown in FIG. 2, the color samples 2 modeling the form of the artificial tooth of the anterior tooth are rotated at an approximately right angle with respect to plate-shaped handle parts 1, and a plurality of the plate-shaped handle parts 1 are stacked for use in many cases. However, in the conventional dental shade guide, since the marks M showing the color tones of the color samples 2 are indicated only at the plate-shaped handle parts 1, there is a problem that only one mark M indicated at the forefront handle part 1 can be confirmed by the photograph.

SUMMARY OF THE INVENTION

The primary objective of the present invention is to provide a dental shade guide, in which teeth and the dental shade guides can be photographed in a large size and particularly when the plurality of the dental shade guides having the different color tones and the teeth of a patient are simultaneously photographed. This dental shade guide can be photographed without making the photograph distance far from the teeth of a patient even when they are photographed so as to put the marks showing the color tones of the color samples within the frame of the photograph. Further, in this dental shade guide, all marks of the dental shade guides can be indicated, even when the color samples are rotated at an approximately right angle with respect to a longitudinal direction of the plate-shaped handle parts so that the plate-shaped handles are stacked for use.

The present invention relates to the dental shade guide, in which a color sample modeling the form of an artificial tooth of the anterior tooth and a tag having a mark indication part are attached at the one end of the plate-shaped handle part rotatably around an axis and the tag is attached at a lingual surface side of the color sample. When this tag is seen from a labial surface side of the color sample, the mark indication part of the tag protrudes 1 to 15 mm at the maximum only from a tooth root directional end or a side of the color sample, so that it can be confirmed. Preferably, in the dental shade guide, the tag is fixed with the color sample in the state that the mark indication part protrudes only from the tooth root directional end of the color sample so as to be confirmed, and the tag and the color sample are attached rotatably together around the axis.

Further, according to the other dental shade guide in the present invention, the color sample has the mark indication part at the tooth root directional end thereof, in which the color sample modeling the form of the artificial tooth of the anterior tooth is attached at the one end of the plate-shaped handle part rotatably around the axis.

The present invention is the dental shade guide, in which the teeth and the dental shade guides can be photographed with large size and particularly when the plurality of the dental shade guides having the different color tones and the teeth of a patient are simultaneously photographed. This dental shade guide can be photographed without making the photograph distance far from the teeth of a patient even when they are photographed so as to put the marks showing the color tones of the color samples within the frame of the photograph. Further, this dental shade guide can indicate all the marks of the dental shade guides, even when the color sample is rotated at the approximately right angle with respect to the longitudinal direction of the plate-shaped handle part so that the plate-shaped handles are stacked for use.

DETAILED DESCRIPTION OF PREFERRED EMBODIMENT

Hereinafter, the dental shade guide according to the present invention is explained concretely with drawings.

Figure 1:
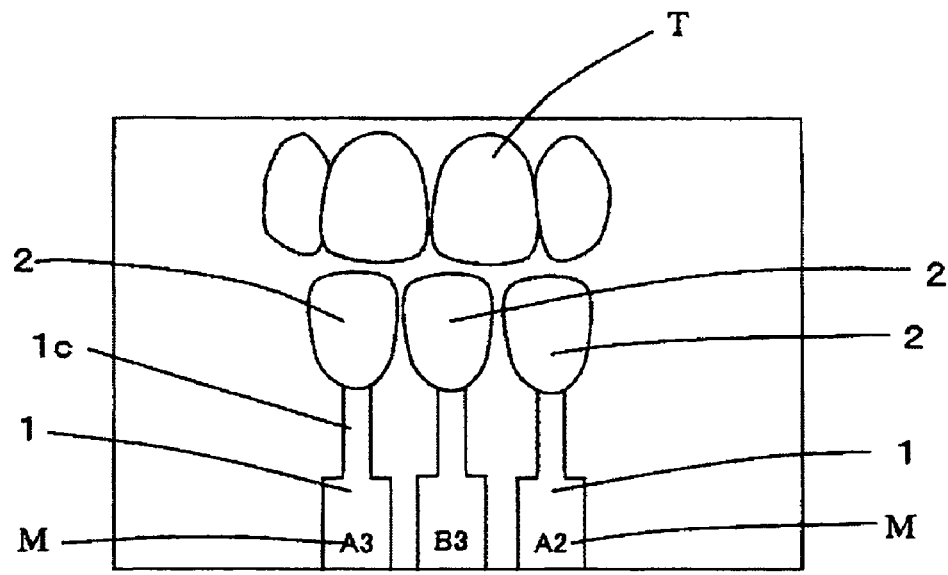
FIG. 1 is an explanation view, which schematically shows a photograph when using a plurality of conventional dental shade guides.
Figure 3A:
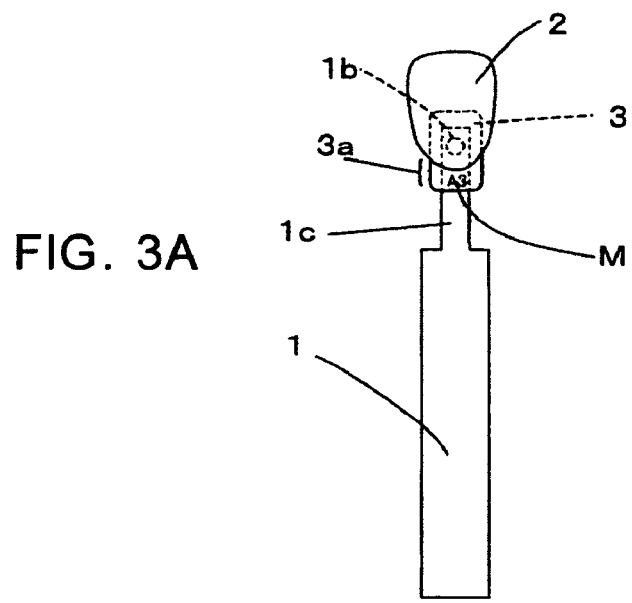
FIG. 3A is a front view showing one example of the dental shade guide according to the present invention.
Figure 3B:
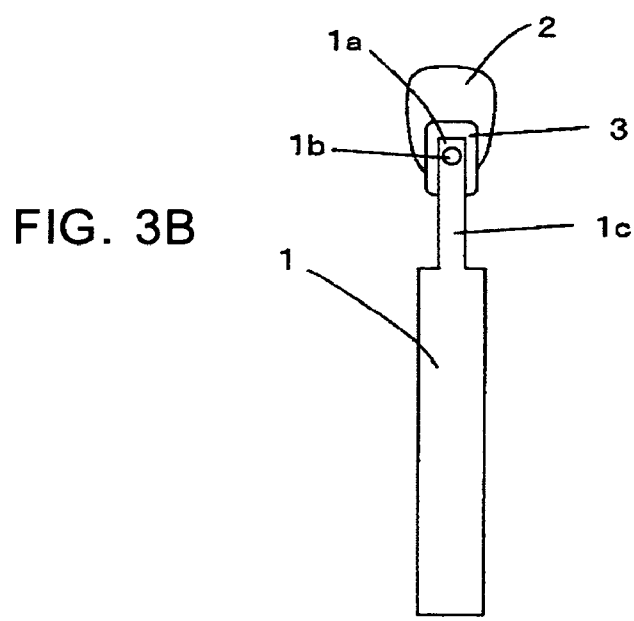
FIG. 3B is a rear face view of the dental shade guide shown in FIG. 3A.

In FIGS. 3A and 3B, 1 is a handle part for handling the dental shade guide when using. Further, the handle part 1 may be an inserting part for inserting it into a holder of the dental shade guide, like the general dental shade guide, as shown in FIG. 1 of published Japanese translations of PCT international publication for patent applications No. 2003-513743 "Dental Prosthesis Shade Guide and Method for Selecting Color Tone of Dental Restoration".

Figure 2:
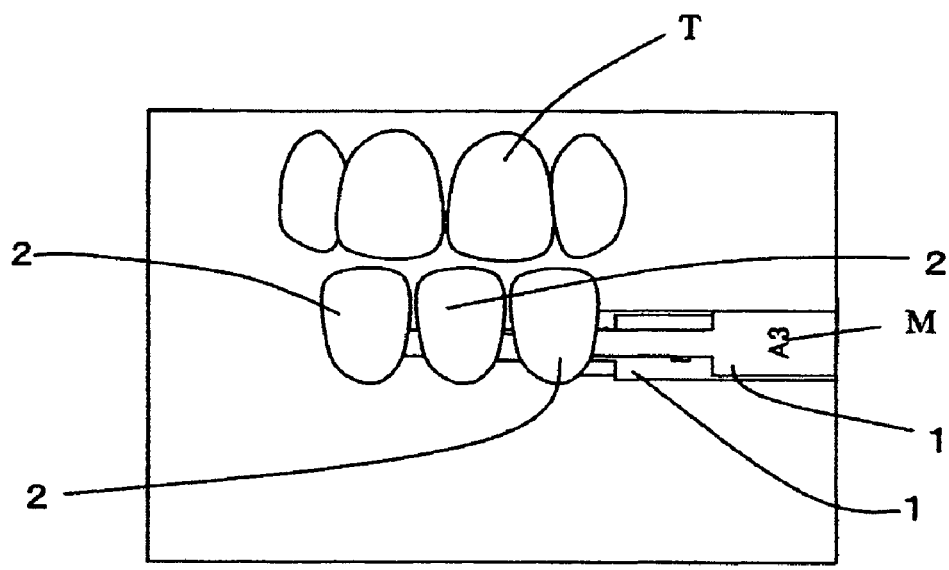
FIG. 2 is an explanation view, which schematically shows a photograph when using a plurality of a conventional dental shade guides, where the color samples are rotated at an approximately right angle with respect to a longitudinal direction of the plate-shaped handle parts so that the plate-shaped handles are stacked for use.

The handle part 1 is a plate-shaped part, and the reason of this shape is as follows. When the teeth and a plurality of the dental shade guide are photographed, for example, as shown in FIG. 2, there are some cases that the color samples 2 modeling the form of the artificial tooth of the anterior tooth are rotated at the approximately right angle with respect to the plate-shaped handle parts 1, where the plate-shaped handle parts 1 are stacked for use. Thus, the handle part 1 is plate-shaped. Further, a neck part 1c which is formed having a thin width may be provided at the handle part 1 like the conventional one.

The color sample 2 modeling the form of the artificial tooth of the anterior tooth, as mentioned below, and a tag 3 having a mark indication part 3a are provided at one end 1a of the plate-shaped handle part 1 rotatably around an axis 1b.

In FIGS. 3A and 3B, 2 is the color sample. The color sample 2 modeling the form of the anterior tooth of the artificial tooth is used in the dental shade guide according to the present invention, since it is possible to indicate the influence to the color tone by the form of the tooth. The color sample 2 is attached rotatably around the axis 1b to the one end 1a of the handle part 1 in a part near the center of gravity. It is possible to fit freely the directions of the handle part 1 with the tooth T of a patient by arbitrarily rotating the color sample 2.

In FIGS. 2 3A and 3B, 3 is the tag. The tag 3 has the mark indication part 3a near a part of at least one end thereof, wherein the mark indication part 3a indicates the color of the color sample 2 with the mark such as a number, alphabet or the like. When the tag 3 has a circular form or the like, an edge of it is used for the mark indication part 3a. The tag 3 is rotatably attached at the lingual surface side rotatably around the axis 1b. That is, the tag 3 and the color sample 2 are rotatably attached respectively centering on the same axis 1b. In addition, the tag 3 may be attached so as to be pinched between the color sample 2 and the handle part 1, or at an opposing side to the color sample 2 of the handle part 1.

Figure 4:
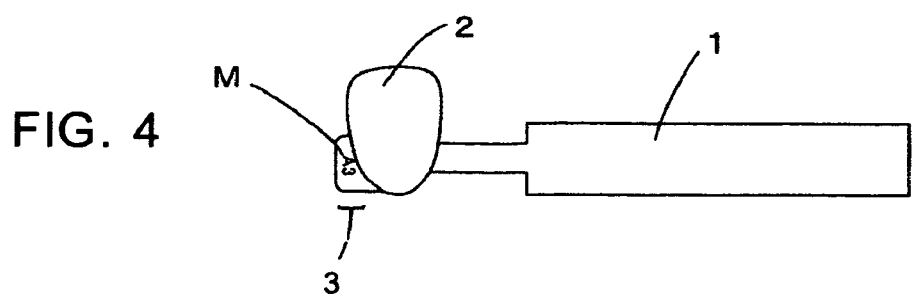
FIG. 4 is a front view showing the state that a color sample of the dental shade guide shown in FIG. 3, but not the tag, is rotated at the approximately right angle with respect to the longitudinal direction of the plate-shaped handle part.

Although the form of the tag 3 is not limited especially, the following forms, for example are preferable. When the mark indication part 3a of the tag 3 is seen from the labial surface side of the color sample 2, as shown in FIG. 3A, the mark indication part 3a at the lingual side of the color sample 2 can be confirmed below the lower part of the color sample 2, i.e. the tooth root directional end of the artificial tooth, over the color sample 2, or as shown in FIG. 4, the mark indication part 3a can be confirmed only at the side of the color sample 2 over the color sample 2. The preferable form of the tag 3 is an ellipse, a square, a rectangle or an approximation form of those.

Figure 5:
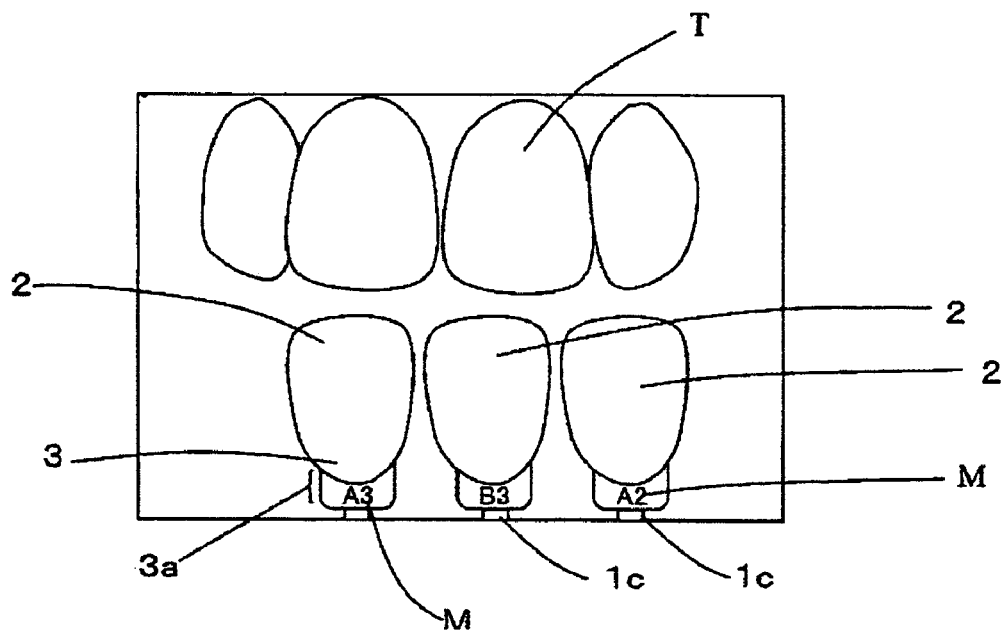
FIG. 5 is an explanation view, which schematically shows the photograph when using a plurality of the dental shade guides shown in FIG. 3.
Figure 6:
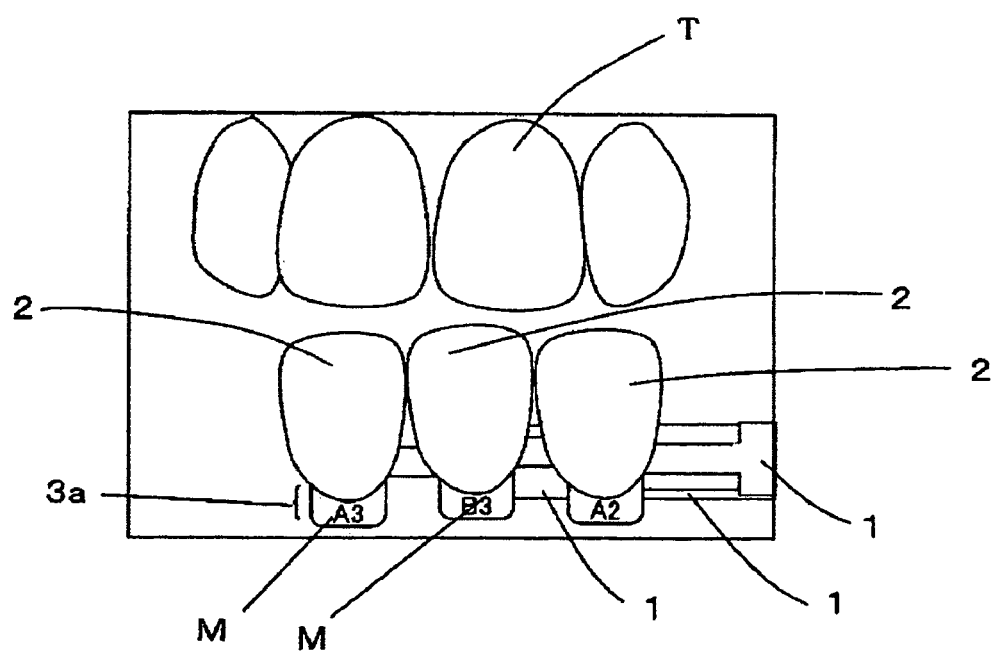
FIG. 6 is an explanation view, which schematically shows the photograph when using a plurality of the dental shade guides shown in FIG. 3, where the color samples are rotated at an approximately right angle with respect to a longitudinal direction of the plate-shaped handle parts so that the plate-shaped handles are stacked for use.

The mark indication part 3a is confirmed when it protrudes 1 to 15 mm at the maximum, preferably 1 to 7 mm, from only the tooth root directional end or side of the color sample 2. The mark M is not confirmed when this part 3a protrudes less than 1 mm. When this part 3a protrudes more than 15 mm, the effect being characteristic of the present invention is lost. That is, the effect that the teeth and the color samples 2 of the dental shade guides can be photographed in a large size and particularly without making the photographing distance far from the teeth T of a patient, when being photographed so as to put the mark M indicating the color tone of the color sample 2 within the frame of the photograph, is lost. In the dental shade guide according to the present invention, when the mark indication part 3a is seen from the labial surface side of the color sample 2, this part 3a protrudes 1 to 15 mm at the maximum, preferably 1 to 7 mm, from only the tooth root directional end or side of the color sample 2, and thus, the mark M indicating the color tone of the color sample 2 can be indicated. Therefore, as compared with the one in FIG. 1 using the dental shade guide in which the mark M is indicated at the handle part, the photographing distance from the teeth T of a patient can be made short, and the teeth T and the color samples 2 of the dental shade guides can be photographed in a large size and particularly (refer to FIG. 5).

As mentioned above, when the tag 3 is rotated around the axis 1b, the mark indication part 3a can be indicated at a left or right side of the color sample 2 over the color sample 2 by choosing the combination of the sizes or forms of the tag 3 and the color sample 2, the attaching positions of those with the axis 1b, or the like. In this way, since the tag 3 is rotatably attached around the axis 1a, the mark indication part 3a can be indicated arbitrarily below the tooth root directional end or at the left or right side of the color sample 2, even when the color sample 2 is directed in the any direction, such as the upper direction, the lower direction or the like, with respect to the direction of the handle part 1.

In the dental shade guide according to the present invention, when the tag 3 is fixed with the color sample 2 in the state that the mark indication part 3a protrudes only from the tooth root directional end of the color sample 2 to be confirmed, and the tag 3 and the color sample 2 are attached rotatably together around the axis 1a, since it is not necessary to move the tag 3 and the color sample 2 respectively, the operatability becomes preferable. So, such the dental shade guide is preferable.

The other dental shade guide according to the present invention is the dental shade guide in which the color sample 2 has the mark indication part 3a at the tooth root directional end. In this dental shade guide, the color sample 2 modeling the form of the artificial tooth of the anterior tooth is attached at the one end 1*a* of the plate-shaped handle part 1 rotatably around the axis 1*b*.

Figure 7:
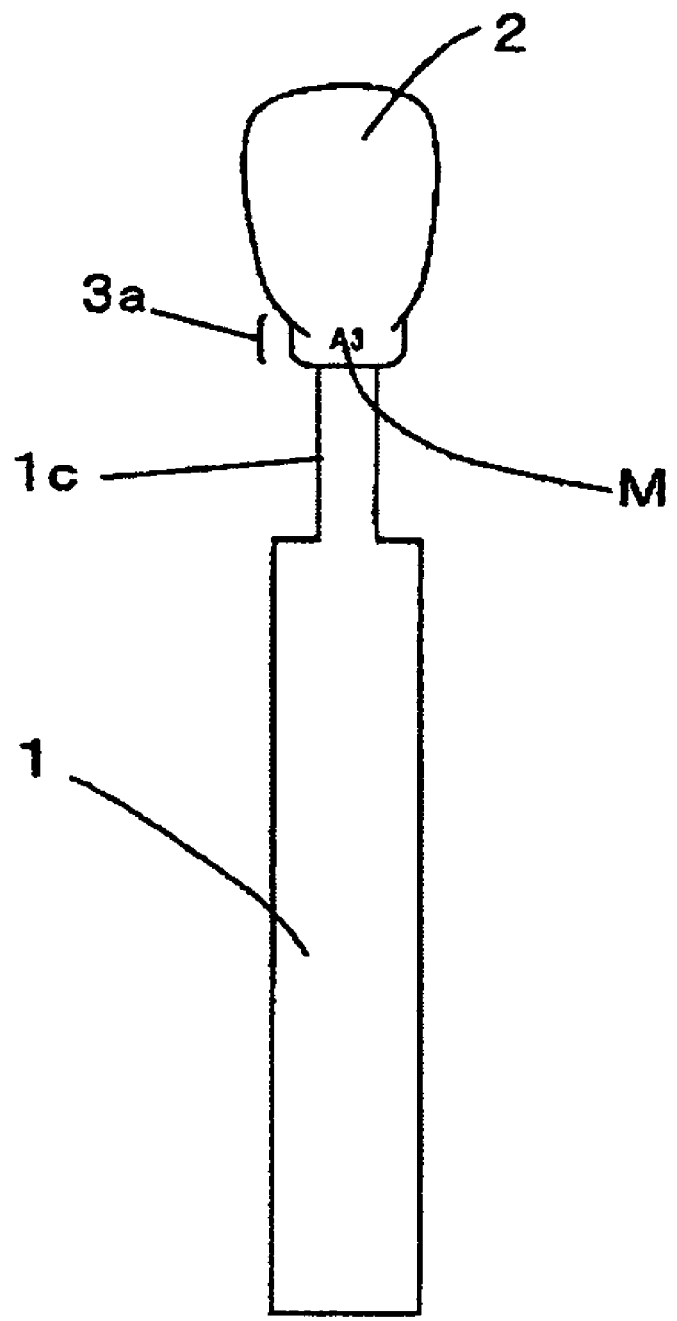
FIG. 7 is a front view showing one example of the other invention of the dental shade guide according to the present invention.

The color sample 2 in this invention has the mark indication part 3*a* indicating with the mark such as a number, alphabet or the like at the tooth root directional end of the color sample 2 modeling the form of the artificial tooth of the anterior tooth, wherein the mark indication. Further, the mark indication part 3*a* may be another member to the color sample 2, or may be integrally formed with the color sample 2 as shown in FIG. 7.

As for the dental shade guide according to the present embodiment, when the teeth T of a patient and the plurality of the dental shade guide are photographed, the mark indication parts 3*a* of the all dental shade guides can be confirmed below or at the tooth root directional ends or at the sides of the color samples 2, even if the color samples 2 are rotated at the approximately right angle with respect to the longitudinal direction of the plate-shaped handle parts so that the plate-shaped handles are stacked for use. Therefore, the problem in the conventional dental shade guide that only the mark M indicated at the forefront handle part 1 can be confirmed by the photograph because the mark M indicating the color tone of the color sample 2 is indicated at the plate-shaped handle part 1 (refer to FIG. 2) is not generated.

What is claimed is:

1. A dental shade guide comprising:
   a color sample modeling a form of an artificial tooth of an anterior tooth;
   a tag having a mark indication part bearing a mark indicative of the color of the color sample; and
   a plate-shaped handle part,
   wherein said color sample, said tag and said handle part are rotatably attached at a common axis passing through said color sample, said tag and said handle part, such that said color sample, said tag and said handle part can rotate about said common axis independently of one another, and
   wherein said tag is attached at a lingual surface side of said color sample, and said mark indication part protrudes 1 to 15 mm at a maximum from a tooth root directional end or a side of said color sample so that it can be confirmed when said mark indication part is seen from a labial surface side of said color sample.

2. The dental shade guide claimed in claim 1, wherein the tag is fixed with the color sample such that the mark indication part protrudes only from the tooth root directional end of the color sample, and said tag and said color sample are attached to rotate together around said axis.

* * * * *